(12) United States Patent
Chiou et al.

(10) Patent No.: US 11,806,088 B2
(45) Date of Patent: Nov. 7, 2023

(54) METHOD, SYSTEM, COMPUTER PROGRAM PRODUCT AND APPLICATION-SPECIFIC INTEGRATED CIRCUIT FOR GUIDING SURGICAL INSTRUMENT

(71) Applicants: CHANG GUNG UNIVERSITY, Taoyuan (TW); Chang Gung Memorial Hospital, Keelung, Keelung (TW)

(72) Inventors: Shin-Yan Chiou, Zhubei (TW); Pin-Yuan Chen, Taoyuan (TW); Hao-Li Liu, Taoyuan (TW); Kuo-Chen Wei, Taoyuan (TW)

(73) Assignees: CHANG GUNG UNIVERSITY, Taoyuan (TW); CHANG GUNG MEMORIAL HOSPITAL, KEELUNG, Keelung (TW)

( * ) Notice: Subject to any disclaimer, the term of this patent is extended or adjusted under 35 U.S.C. 154(b) by 91 days.

(21) Appl. No.: 17/217,419

(22) Filed: Mar. 30, 2021

(65) Prior Publication Data

US 2021/0386483 A1 Dec. 16, 2021

(30) Foreign Application Priority Data

Jun. 10, 2020 (TW) .................................. 109119432

(51) Int. Cl.
*A61B 34/20* (2016.01)
*A61B 34/00* (2016.01)
(Continued)

(52) U.S. Cl.
CPC .............. *A61B 34/20* (2016.02); *A61B 34/25* (2016.02); *A61B 90/39* (2016.02); *G06T 7/30* (2017.01);
(Continued)

(58) Field of Classification Search
CPC . A61B 34/20; A61B 34/25; A61B 2034/2065; A61B 2034/2055;
(Continued)

(56) References Cited

U.S. PATENT DOCUMENTS

2013/0060146 A1* 3/2013 Yang ...................... G01B 11/25
600/476
2019/0380792 A1* 12/2019 Poltaretskyi ......... H04N 13/332
(Continued)

FOREIGN PATENT DOCUMENTS

| CN | 102525660 A | 7/2012 |
|----|-------------|--------|
| CN | 106974730 | 7/2017 |

(Continued)

OTHER PUBLICATIONS

Search Report appended to an Office Action, which was issued to Taiwanese counterpart application No. 109119432 by the TIPO dated Nov. 10, 2020 with an English translation thereof.

*Primary Examiner* — Colin T. Sakamoto
*Assistant Examiner* — Tommy T Ly
(74) *Attorney, Agent, or Firm* — Fox Rothschild LLP

(57) ABSTRACT

A method includes providing medical images of a subject for selecting a target image from thereamong, building a 3D image model based on the medical images and the target image with a surgical target site assigned, performing image registration to superimpose the 3D image model on a real-time image of the subject so as to result in a combined image, determining a virtual entry site located on the combined image, connecting the surgical target site and the virtual entry site with a straight line, generating a guiding path extending from the virtual entry site, in a direction away from the surgical target site and along the straight line, and displaying the guiding path for guiding a surgical instrument.

20 Claims, 8 Drawing Sheets

(51) Int. Cl.
*A61B 34/10* (2016.01)
*G06T 7/30* (2017.01)
*A61B 90/00* (2016.01)

(52) U.S. Cl.
CPC ... *A61B 2034/102* (2016.02); *A61B 2034/107* (2016.02); *A61B 2034/108* (2016.02); *A61B 2034/2065* (2016.02)

(58) Field of Classification Search
CPC ........ A61B 2034/105; A61B 2034/107; A61B 34/10; A61B 2034/102; A61B 6/461; A61B 8/461; A61B 2090/365
See application file for complete search history.

(56) References Cited

U.S. PATENT DOCUMENTS

| | | | |
|---|---|---|---|
| 2020/0060767 A1* | 2/2020 | Lang | A61B 17/1742 |
| 2020/0085511 A1* | 3/2020 | Oezbek | H04N 13/332 |
| 2020/0242830 A1* | 7/2020 | Bharadwaj | A61B 90/10 |
| 2020/0375664 A1* | 12/2020 | Tang | A61B 6/12 |

FOREIGN PATENT DOCUMENTS

| | | |
|---|---|---|
| CN | 110650703 | 1/2020 |
| TW | 202000143 | 1/2020 |
| WO | WO-2021214754 A1 * | 10/2021 |

\* cited by examiner

METHOD, SYSTEM, COMPUTER PROGRAM PRODUCT AND APPLICATION-SPECIFIC INTEGRATED CIRCUIT FOR GUIDING SURGICAL INSTRUMENT

CROSS-REFERENCE TO RELATED APPLICATION

This application claims priority of Taiwanese Invention Patent Application No. 109119432, filed on Jun. 10, 2020.

FIELD

The disclosure relates to a method, a system, a computer program product and an application-specific integrated circuit (ASIC) for guiding a surgical instrument.

BACKGROUND

Conventionally, before performing a surgical treatment on a subject, a surgical target site (e.g., a lesion in the brain of the subject with hydrocephalus) has to be determined with the assistance of techniques such as optical navigation, augmented reality (AR) or mixed reality (MR) based on medical images obtained by using computed tomography (CT), magnetic resonance imaging (MRI) or ultrasound imaging. However, quantitative information in medical images that follow Digital Imaging and Communications in Medicine (DICOM) standards cannot be displayed in real time by a conventional surgical navigation system when a medical professional (e.g., a doctor or a surgeon) is performing the surgical treatment. Therefore, the medical professional has to determine a movement path of the surgical instrument from an entry site (i.e., a site on a body part of the subject into which a surgical instrument is to be inserted at the beginning of surgery) to the surgical target site by himself/herself based on his/her personal experiences.

SUMMARY

Therefore, an object of the disclosure is to provide a method, a system, a computer program product and an application-specific integrated circuit (ASIC) for guiding a surgical instrument that can alleviate at least one of the drawbacks of the prior art.

According to one aspect of the disclosure, the method is to be implemented by a system. The method includes:
  providing a plurality of medical images which are related to a subject for selection of one medical image from among the plurality of medical images as a target image, and displaying the target image, the target image containing an image portion which represents a lesion of the subject and on which a surgical target site is to be assigned;
  building, based on the medical images and the target image with the surgical target site assigned, a three-dimensional (3D) image model which corresponds to the subject and which is marked with the surgical target site;
  capturing a real-time image of the subject, performing image registration to superimpose the 3D image model on the real-time image so as to result in a combined image which is marked with the surgical target site, and displaying the combined image; and
  determining, based on the medical images and the surgical target site marked on the combined image, a virtual entry site that is located on the combined image and that corresponds to an actual entry site on the subject, connecting the surgical target site and the virtual entry site with a straight line, generating a guiding path extending from the virtual entry site, in a direction away from the surgical target site and along the straight line, and displaying the guiding path for guiding the surgical instrument.

According to another aspect of the disclosure, the system includes a display, a storage, an image capturing device, and a processor electrically connected to the storage, the display and the image capturing device.

The storage is configured to store a plurality of medical images which are related to a subject.

The image capturing device is configured to capture a real-time image of the subject.

The processor is configured to select one medical image from among the plurality of medical images as a target image and to display the target image via the display. The target image contains an image portion which represents a lesion of the subject.

The processor is further configured to, based on a user selection inputted via a graphical user interface (GUI), assign a surgical target site on the image portion of the target image.

The processor includes a model-building module, an image-registration module and a guiding-line-generating module.

The model-building module is configured to build, based on the medical images, a 3D image model which corresponds to the subject and which is marked with the surgical target site.

The image-registration module is configured to determine whether the real-time image is being displayed via the display, to perform, when it is determined that the real-time image is being displayed via the display, image registration to superimpose the 3D image model on the real-time image so as to result in a combined image which is marked with the surgical target site, and to display the combined image via the display.

The guiding-line-generating module is configured to determine, based on the medical images stored in the storage and the surgical target site marked on the combined image, a virtual entry site that is located on the combined image and that corresponds to an actual entry site on the subject, to connect the surgical target site and the virtual entry site with a straight line, to generate a guiding path extending from the virtual entry site, in a direction away from the surgical target site and along the straight line, and display the guiding path via the display for guiding the surgical instrument.

According to still another aspect of the disclosure, the computer program product includes a non-transitory computer readable storage medium having program instructions stored therewith. The program instructions constitute a model-building module, an image-registration module and a guiding-line-generating module. The program instructions are executable by a system to cause the system to:
  provide a plurality of medical images which are related to a subject for selection of one medical image from among the plurality of medical images as a target image, and display the target image, the target image containing an image portion which represents a lesion of the subject and on which a surgical target site is to be assigned;
  build, by the model-building module based on the medical images and the target image with the surgical target site assigned, a 3D image model which corresponds to the subject and which is marked with the surgical target site;

capture a real-time image of the subject;

by the image-registration module, perform image registration to superimpose the 3D image model on the real-time image so as to result in a combined image which is marked with the surgical target site, and display the combined image; and by the guiding-line-generating module, determine, based on the medical images and the surgical target site marked on the combined image, a virtual entry site that is located on the combined image and that corresponds to an actual entry site on the subject, connect the surgical target site and the virtual entry site with a straight line, generate a guiding path extending from the virtual entry site in a direction away from the surgical target site and along the straight line, and display the guiding path for guiding the surgical instrument.

According to further another aspect of the disclosure, the ASIC includes a model-building module, an image-registration module and a guiding-line-generating module. The ASIC is utilized by an electronic device to cause the electronic device to:

provide a plurality of medical images which are related to a subject for selection of one medical image from among the plurality of medical images as a target image, and display the target image, the target image containing an image portion which represents a lesion of the subject and on which a surgical target site is to be assigned;

build, by the model-building module based on the medical images and the target image with the surgical target site assigned, a 3D image model which corresponds to the subject and which is marked with the surgical target site;

capture a real-time image of the subject;

by said image-registration module, perform image registration to superimpose the 3D image model on the real-time image so as to result in a combined image which is marked with the surgical target site, and display the combined image; and by said guiding-line-generating module, determine, based on the medical images and the surgical target site marked on the combined image, a virtual entry site that is located on the combined image and that corresponds to an actual entry site on the subject, connect the surgical target site and the virtual entry site with a straight line, generate a guiding path extending from the virtual entry site in a direction away from the surgical target site and along the straight line, and display the guiding path for guiding the surgical instrument.

BRIEF DESCRIPTION OF THE DRAWINGS

Other features and advantages of the disclosure will become apparent in the following detailed description of the embodiments with reference to the accompanying drawings, of which.

DETAILED DESCRIPTION

Figure 1:
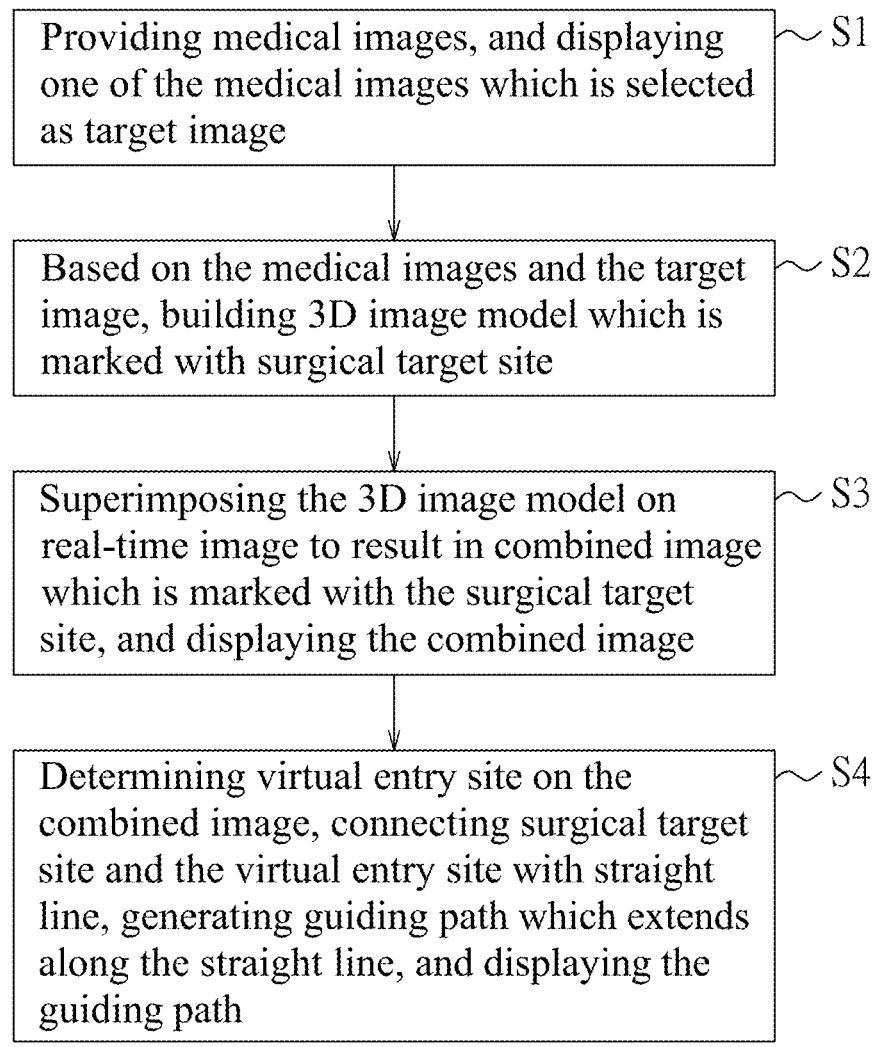
FIG. 1 is a flow chart illustrating an embodiment of a guide-line-generating procedure of a method for guiding a surgical instrument according to the disclosure.

Before the disclosure is described in greater detail, it should be noted that where considered appropriate, reference numerals or terminal portions of reference numerals have been repeated among the figures to indicate corresponding or analogous elements, which may optionally have similar characteristics.

Figure 3:
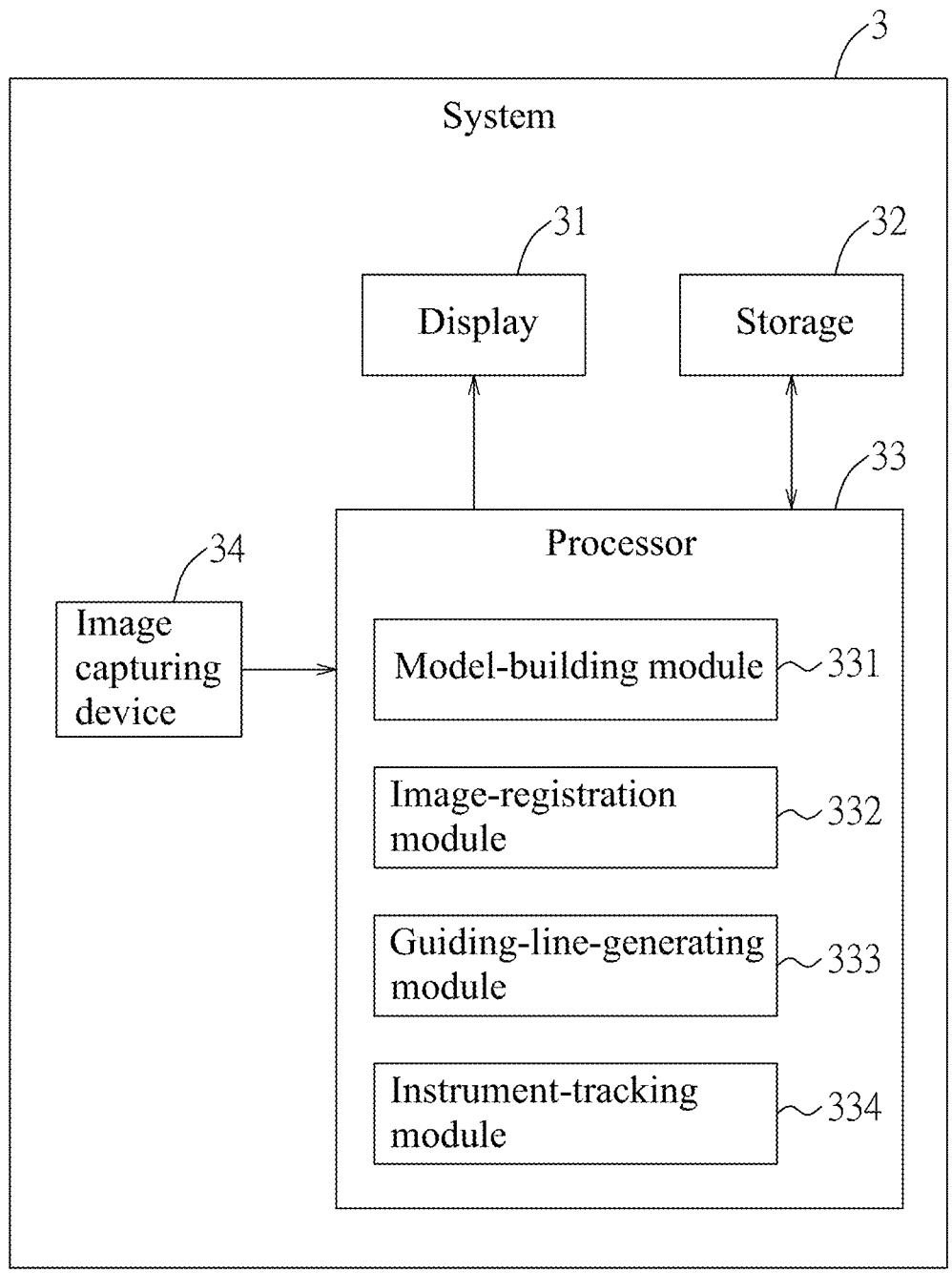
FIG. 3 is a block diagram illustrating an embodiment of a system for guiding a surgical instrument according to the disclosure.

Referring to FIG. 3, an embodiment of a system 3 for guiding a surgical instrument 7 (see FIG. 6) according to the disclosure is illustrated. In this embodiment, the system 3 may be implemented by a desktop computer, a laptop computer, a notebook computer, a tablet computer, a smartphone or a head-mounted display (e.g., augmented reality (AR) glasses or an AR headset). However, implementation of the system is not limited to the disclosure herein and may vary in other embodiments.

The system 3 includes a display 31, a storage 32, an image capturing device 34, and a processor 33 electrically connected to the storage 32, the display 31 and the image capturing device 34.

In this embodiment, the display 31 may be a liquid-crystal display (LCD), a light-emitting diode (LED) display, a plasma display panel, a projection display or the like. However, implementation of the display 31 is not limited to the disclosure herein and may vary in other embodiments.

Figure 6:
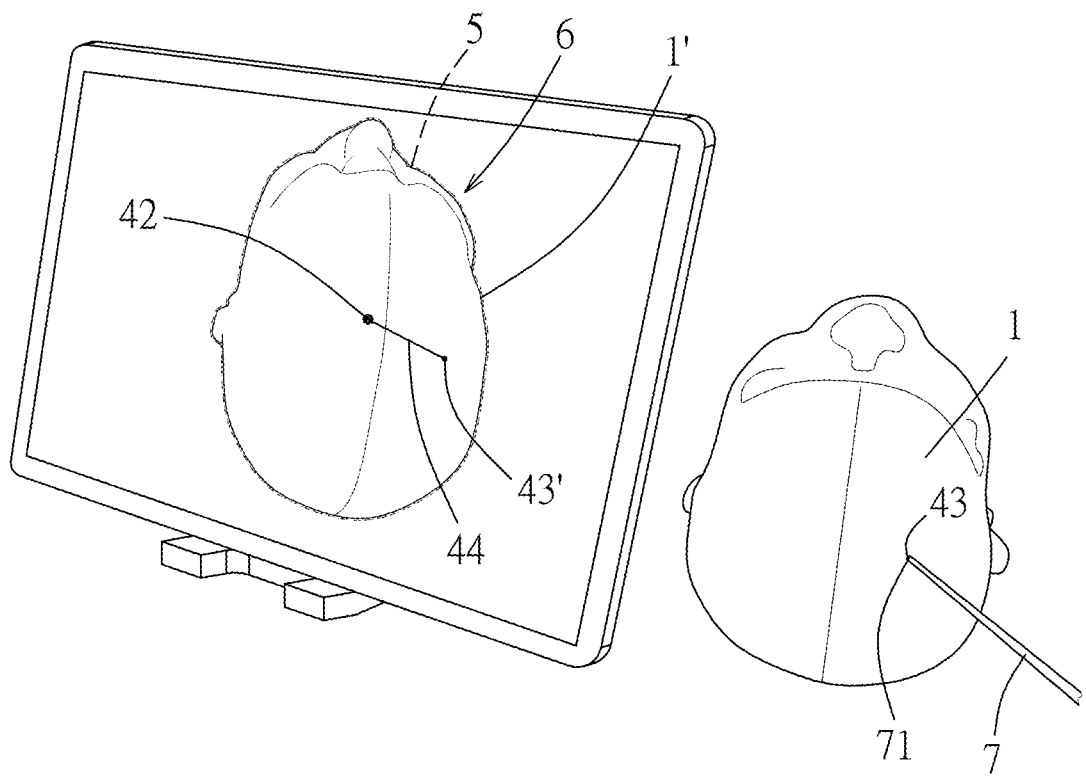
FIG. 6 is a schematic diagram illustrating an embodiment of superimposing the 3D image model on a real-time image to result in a combined image by the system according to the disclosure.

The storage 32 is configured to store a plurality of medical images which are related to a subject 1 (see FIG. 6). The subject 1 may be the head of a human. In this embodiment, the storage 32 may be implemented by flash memory, a hard disk drive (HDD) or a solid state disk (SSD), electrically-erasable programmable read-only memory (EEPROM) or any other non-volatile memory devices, but is not limited thereto. The medical images may be cross-sectional images obtained by using computed tomography (CT), magnetic resonance imaging (MRI) or ultrasound imaging, and may contain information of blood vessels, nerves and/or bones.

Moreover, management (e.g., storage, processing, transmission and so on) of the medical images follows standards of Digital Imaging and Communications in Medicine (DICOM).

The image capturing device 34 is configured to capture a real-time image 1' (see FIG. 6) of the subject 1. In this embodiment, the image capturing device 34 may be implemented by a camera or a video recorder, but is not limited thereto. The real-time image 1' is provided to the processor 33, and is displayed in real-time on the display 31.

In this embodiment, the processor 33 may be implemented by a central processing unit (CPU), a microprocessor, a micro control unit (MCU), a system on a chip (SoC), or any circuit configurable/programmable in a software manner and/or hardware manner to implement functionalities discussed in this disclosure.

The processor 33 includes a model-building module 331, an image-registration module 332, a guiding-line-generating module 333 and an instrument-tracking module 334. It should be noted that in this embodiment, the aforementioned modules may be implemented by one of hardware, firmware, software, and any combination thereof. For example, these modules may be implemented to be software modules in a program, where the software modules contain codes and instructions to carry out specific functionalities, and can be called individually or together to fulfill operations of the system 3 of this disclosure.

Figure 4:
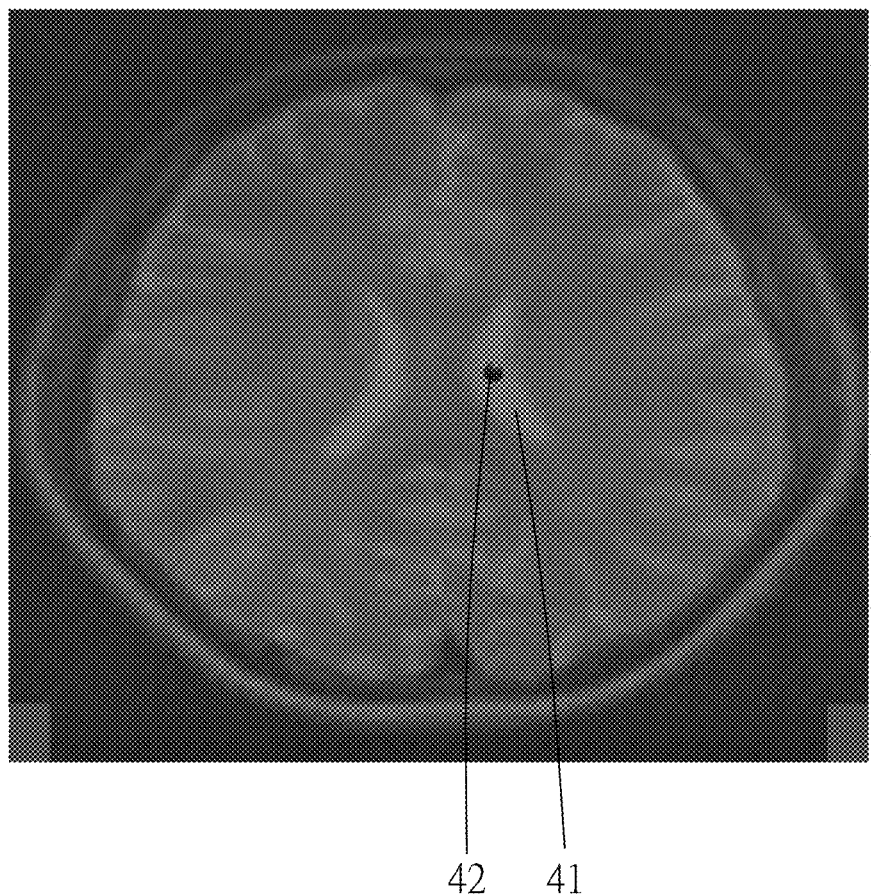
FIG. 4 is a schematic diagram illustrating an embodiment of a target image selected by the system according to the disclosure.

The processor 33 is configured to, based on user operations, select one medical image from among the plurality of medical images as a target image as shown in FIG. 4 and to display the target image via the display 31. The target image contains an image portion 41 which represents a lesion of the subject 1. The processor 33 is further configured to, based on a user selection inputted via a graphical user interface (GUI) (not shown), assign a surgical target site 42 on the image portion 41 of the target image. The lesion of the subject 1 may be a site where cerebrospinal fluid is accumulating in the brain of the subject 1 with hydrocephalus, and requires treatment by surgery to drain the fluid. The processor 33 is further configured to determine whether a surgical target site 42 is assigned on the image portion 41 of the target image, and when it is determined that a surgical target site 42 is assigned on the image portion 41 of the target image, to control the display 31 to mark the surgical target site 42 on the image portion 41.

In one embodiment, the processor 33 is configured to utilize an artificial intelligence module (not shown), e.g., a neural network model that has been trained, to automatically select one medical image which contains the image portion 41 representing the lesion from among the plurality of medical images as the target image, and to automatically assign the surgical target site 42 on the image portion 41. Thereafter, a medical professional (e.g., a doctor or a surgeon) may directly accept the assignment of the surgical target site 42 or adjust location of the surgical target site 42.

Figure 5:
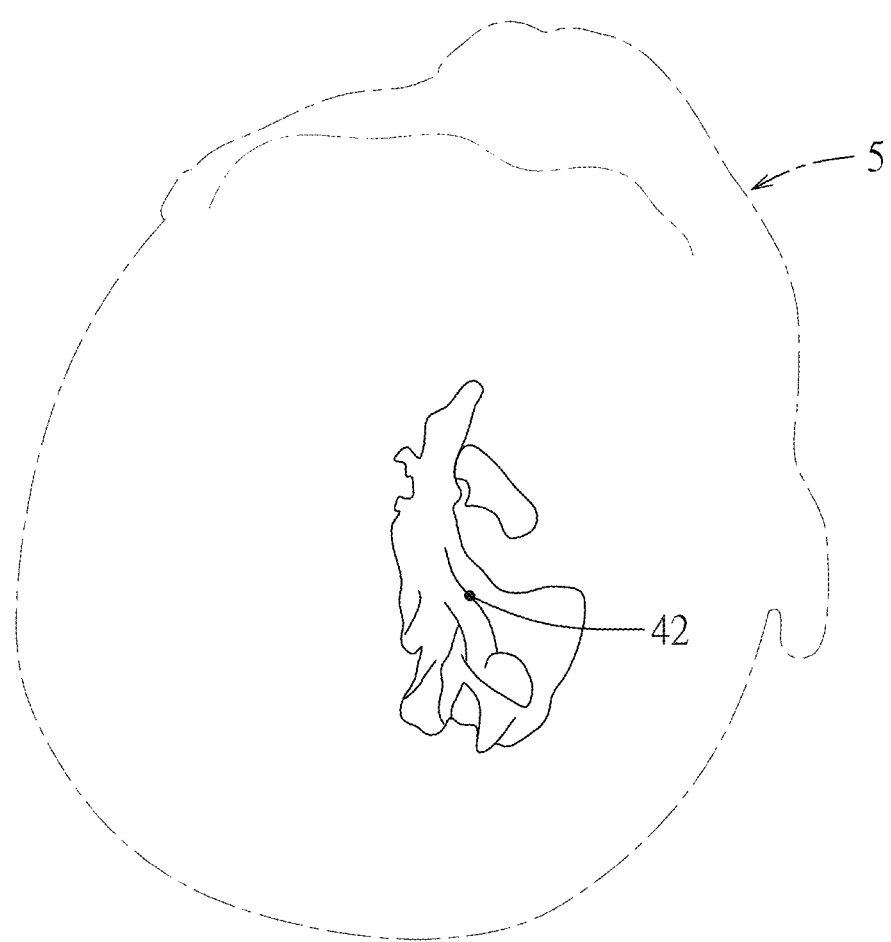
FIG. 5 is a schematic diagram illustrating an embodiment of a three-dimensional (3D) image model built by the system according to the disclosure.

The model-building module 331 is configured to build, based on the medical images and the target image with the surgical target site 42 already assigned, a 3D image model 5 (see FIG. 5) which corresponds to the subject 1 and which is marked with the surgical target site 42.

Specifically speaking, the model-building module 331 is configured to build, based on the plurality of medical images, a first 3D model that represents an anatomical structure of the subject 1, and to build a second 3D model that represents the surgical target site 42 on the lesion based on the image portion 41 contained in the target image, the surgical target site 42 assigned on the target image and the plurality of medical images. The first 3D model and the second 3D model cooperatively serve as the 3D image model 5. In this embodiment, the 3D image model 5 may be built by using Unity, which is a 3D software developed by Unity Technologies. However, building the 3D image model 5 is not limited to the disclosure herein and may vary in other embodiments.

The image-registration module 332 is configured to determine whether the real-time image 1' is being displayed via the display 31, and to perform, when it is determined that the real-time image 1' is being displayed via the display 31, image registration to superimpose the 3D image model 5 on the real-time image 1' so as to result in a combined image 6 which is marked with the surgical target site 42. More specifically, the image-registration module 332 is configured to superimpose the first 3D model and the second 3D model on the real-time image 1' by using image registration techniques so as to result in the combined image 6. Then, the image-registration module 332 is configured to display the combined image 6 via the display 31, thereby facilitating the medical professional to find an actual site in the subject 1 that corresponds to the surgical target site 42 and that is a target location of surgery. It is noted that since the real-time image 1' is captured and displayed in real time and since the combined image 6 is obtained by superimposing the 3D image model 5 onto the real-time image 1', the combined image 6 thus displayed can also reflect a real-time condition of the subject 1.

In this embodiment, performance of image registration may be realized by, but is not limited to, an optical tracking system such as the Polaris Vicra optical tracking system and the Polaris Spectra optical tracking system produced by Northern Digital Inc. (NDI), the ART tracking system produced by Advanced Realtime Tracking GmbH, or the MicronTracker produced by ClaroNav Inc., or may be realized by an image positioning system released by Vuforia augmented reality (AR) platform. Since image registration techniques have been well known to one skilled in the relevant art, detailed explanation of the same is omitted herein for the sake of brevity.

Figure 7:
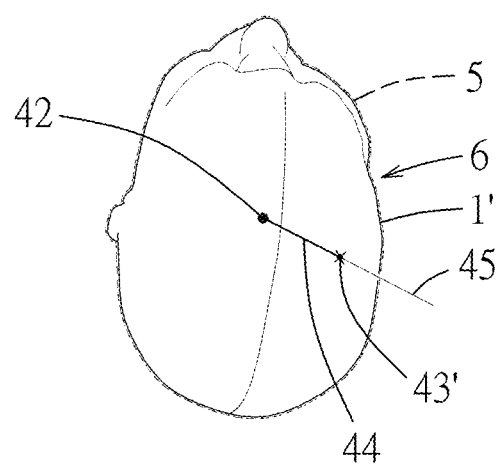
FIG. 7 is a schematic diagram illustrating an embodiment of a guiding path generated by the system according to the disclosure.

Further referring to FIG. 6, the guiding-line-generating module 333 is configured to determine, based on the medical images stored in the storage 32 and the surgical target site 42 marked on the combined image 6, a virtual entry site 43' that is located on the combined image 6 and that corresponds to an actual entry site 43 on an exterior of the subject 1. It should be noted that the actual entry site 43 is a site on a body part of the subject 1 into which the surgical instrument 7 is to be inserted at the beginning of surgery (i.e., an entry point of the surgical instrument 7 into the subject 1). Next, the guiding-line-generating module 333 is configured to connect the surgical target site 42 and the virtual entry site 43' with a straight line 44, and to generate a guiding path 45 (see FIG. 7) extending from the virtual entry site 43', in a direction away from the surgical target site 42 and along the straight line 44. Subsequently, the guiding-line-generating module 333 is configured to display the straight line 44 and the guiding path 45 in the combined image 6 via the display 31 for guiding the surgical instrument 7. In this embodiment, the guiding path 45 may be represented as a thin straight line, a solid circular rod, or a solid circular cone.

It is worth to note that in one embodiment, the virtual entry site 43' is determined based on a result of determination of the actual entry site 43 made by the medical professional. More specifically, the medical professional would determine the actual entry site 43 on the subject 1 based on his/her professional experiences and/or the surgical target site 42 marked on the combined image 6. Subsequently, the medical professional would puncture the actual entry site 43 on the subject 1 using the tip 71 of the instrument 7 as shown in FIG. 6. Next, the guiding-line-generating module 333 determines the virtual entry site 43' in the combined image 6 based on an image of the subject 1 which is punctured at the actual entry site 43 by the tip 71.

It is worth to note that the medical professional is able to change the location of the actual entry site 43 at his/her discretion after referring to the guiding path 45 generated by the guiding-line-generating module 333. That is to say, when the medical professional has decided on a new actual entry site (e.g., by puncturing thereat), the guiding-line-generating module 333 determines a new virtual entry site corresponding to the new actual entry site in the combined image 6, and generates a new guiding path based on the surgical target site 42 and the new virtual entry site.

In one embodiment, the guiding-line-generating module 333 determines the virtual entry site 43' by using techniques of artificial intelligence (e.g., by using a neural network model that has been trained in advance for deciding a virtual entry site).

In one embodiment, the system. 3 records information of the 3D image model 5, the combined image 6 and the guiding path 45.

Figure 8:
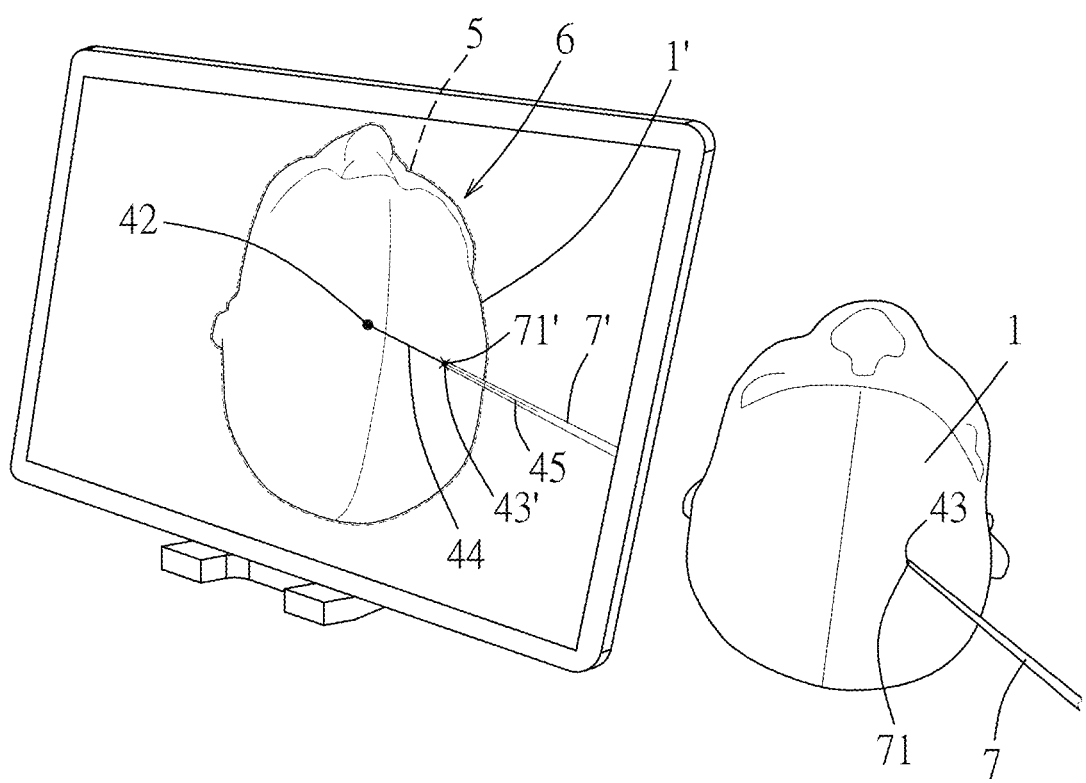
FIG. 8 is a schematic diagram illustrating an embodiment of displaying an instrument image of the surgical instrument in the combined image generated by the system according to the disclosure.

The instrument-tracking module 334 is configured to determine whether an instrument image 7' (see FIG. 8) of the surgical instrument 7 captured by the image capturing device 34 appears in the combined image 6 (that is, whether the surgical instrument 7 enters the field of view of the image capturing device 34). When it is determined that the instrument image 7' appears in the combined image 6, the instrument-tracking module 334 is configured to make a first determination as to whether a tip 71' (see FIG. 8) of the instrument image 7' lies on the virtual entry site 43', to make a second determination as to whether the tip 71' of the instrument image 7' moves along the straight line 44 to reach the surgical target site 42, to make a third determination as to whether a longitudinal axis of the instrument image 7' lies on the guiding path 45, to make a fourth determination as to whether the instrument image 7' moves along the guiding path 45, and to generate feedback based on any one of results of the first, second, third and fourth determinations.

It is worth to note that while making the first, second, third and fourth determinations, the instrument-tracking module 334 utilizes the optical tracking system or the image positioning system that is previously mentioned to obtain information of spatial coordinates of the surgical instrument 7 in real time. In this way, the instrument-tracking module 334 is capable of locating the surgical instrument 7 held by the medical professional, and determining a location of the tip 71 and an orientation of the surgical instrument 7.

When it is determined by the instrument-tracking module 334 that the instrument image 7' appears in the combined image 6, the model-building module 331 is configured to generate a virtual instrument (not shown) that corresponds to the surgical instrument 7, and to control the display 34 to display, in the combined image 6 based on spatial coordinates of the surgical instrument 7 relative to the subject 1, the virtual instrument that is placed at a location where the instrument image 7' appears. Then, the instrument-tracking module 334 is configured to make the aforementioned first, second, third and fourth determinations, and to generate feedback based on any one of the results of the first, second, third and fourth determinations.

In this embodiment, the feedback thus generated includes one of visual feedback, audio feedback, tactile feedback and combinations thereof. However, implementation of the feedback is not limited to the disclosure herein and may vary in other embodiments.

In this embodiment, the visual feedback includes at least one of a color transition of an indicator and a message pop-up. For example, in one embodiment, when it is determined that the tip 71' of the instrument image 7' lies on the virtual entry site 43', the instrument-tracking module 334 controls the display 31 to show a circular indicator 9 (see FIG. 9), for example, on an upper right corner of a screen of the display 31. The circular indicator 9 is used to indicate a relative position of the surgical instrument 7 with respect to the guiding path 45. More specifically, the circular indicator 9 has a central point 91, and a line segment 92 that extends from the central point 91 and that represents a deviation of the surgical instrument 7 from the guiding path 45. In particular, the length of the line segment 92 represents a level of deviation of the surgical instrument 7 from the guiding path 45, and the direction in which the line segment 92 extends represents the direction in which the surgical instrument 7 deviates from the guiding path 45.

Figure 9:
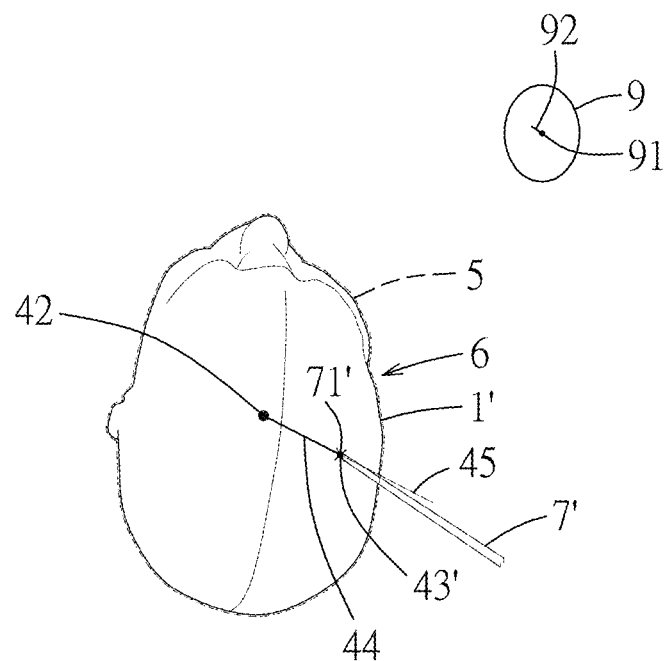
FIG. 9 is a schematic diagram illustrating an embodiment of visual feedback indicating that a longitudinal axis of a virtual instrument does not lie on the guiding path.
Figure 10:
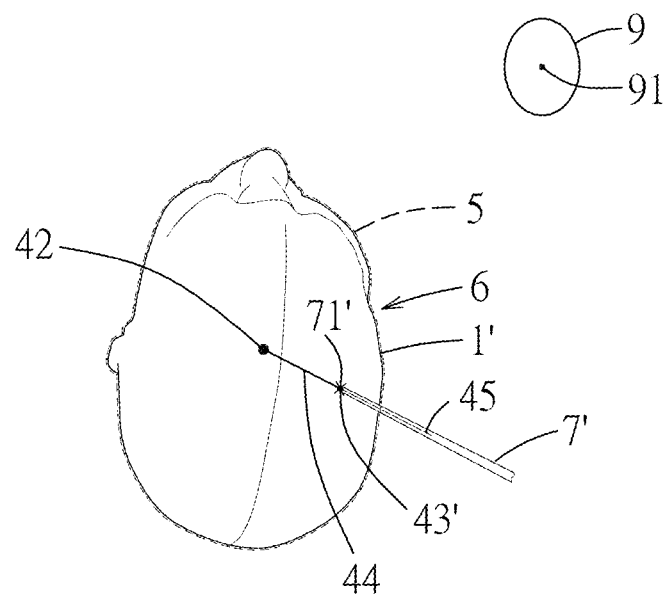
FIG. 10 is a schematic diagram illustrating an embodiment of visual feedback indicating that the longitudinal axis of the virtual instrument lies on the guiding path.

When it is determined that the longitudinal axis of the instrument image 7' lies on the guiding path 45, the instrument-tracking module 334 controls the display 31 to present the circular indicator 9 as shown in FIG. 10 which simply has the central point 91. On the other hand, when it is determined that the longitudinal axis of the instrument image 7' does not lie on the guiding path 45, the instrument-tracking module 334 controls the display 31 to present the circular indicator 9 as shown in FIG. 9 which has both the central point 91 and the line segment 92. By observing the circular indicator 9 presented on the display 31, the medical professional will be notified as to whether the surgical instrument 7 is appropriately positioned and moved in the manner of exactly following the guidance (e.g., the straight line 44, the guiding path 45 and the circular indicator 9) provided by the system 3 according to the disclosure, and will be able to adjust the position and the movement of the surgical instrument 7 accordingly.

In this embodiment, the audio feedback includes playback of a sound notification. For example, the processor 33 is configured to control a speaker (not shown) of the system 3 to output sound notifications such as "The surgical instrument has deviated from the guiding path," "The surgical instrument is approaching the guiding path," and "The surgical instrument lies on the guiding path." Based on the sound notifications thus outputted, the medical professional will be notified as to whether the surgical instrument 7 is appropriately positioned and moved in the manner of exactly following the guidance provided by the system 3 according to the disclosure, and will be able to adjust the position and the movement of the surgical instrument 7 accordingly.

In this embodiment, the tactile feedback includes vibrations emitted by a portable device (not shown). For example, the processor 33 is configured to transmit, via an information transmission interface of the system 3 by means of wired or wireless communication, a feedback signal to the wearable device worn by the medical professional so as to enable the portable device to vibrate. The portable device may be a smartphone placed in a pocket on the medical professional, a smartwatch, a smart bracelet or a wearable beacon worn on one wrist of the medical professional, a control rod that is similar to a Wii Remote Controller and that is held by the medical professional, a smart necklace or smart glasses worn by the medical professional. Sensing vibrations emitted by the wearable device, the medical professional will be notified as to whether the surgical instrument 7 is appropriately positioned and moved in the manner of exactly following the guidance provided by the system 3 according to the disclosure, and will be able to adjust the position and the movement of the surgical instrument 7 accordingly.

In one embodiment, a computer program product for guiding a surgical instrument 7 includes a non-transitory computer readable storage medium having program instructions stored therewith. The program instructions constitute the model-building module 331, the image-registration module 332, the guiding-line-generating module 333 and the instrument-tracking module 334. The program instructions are executable by an electronic device to cause the electronic device to fulfill functionalities disclosed by this disclosure.

In one embodiment, an application-specific integrated circuit (ASIC) for guiding a surgical instrument 7 is configured to constitute the model-building module 331, the image-registration module 332, the guiding-line-generating module 333 and the instrument-tracking module 334. The ASIC is utilized by an electronic device to cause the electronic device to fulfill functionalities disclosed by this disclosure.

Figure 2:
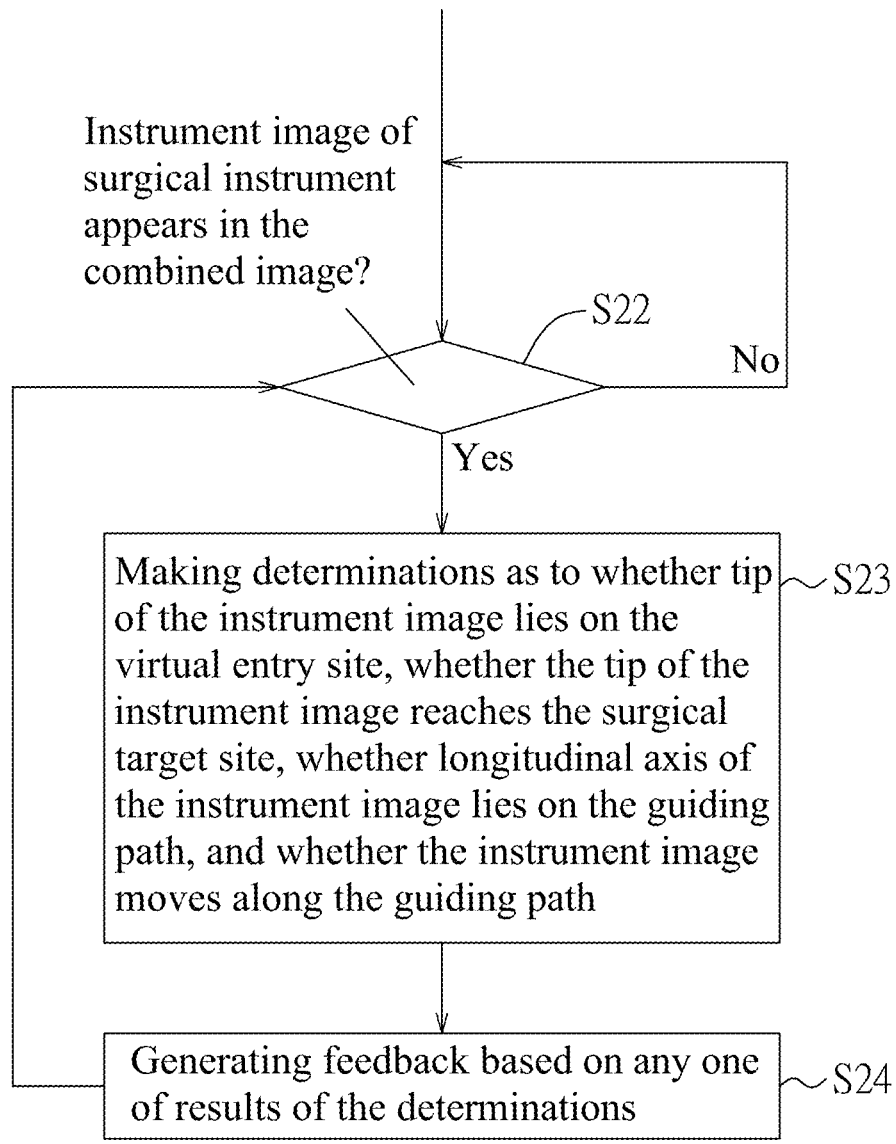
FIG. 2 is a flow chart illustrating an embodiment of an instrument-tracking procedure of the method according to the disclosure.

Referring to FIGS. 1 and 2, an embodiment of a method for guiding a surgical instrument 7 according to the disclosure is illustrated. The method is to be implemented by the system 3 that is previously described. The method according to the disclosure includes a guiding-line-generating procedure and an instrument-tracking procedure.

The guiding-line-generating procedure includes steps S1 to S4 as delineated below.

In step S1, the processor 33 provides the medical images which are related to the subject 1 for selection of one medical image from among the medical images as the target image, and displays the target image. The surgical target site 42 is to be assigned on the target image.

In step S2, the model-building module 331 builds, based on the medical images and the target image with the surgical target site 42 already assigned, the 3D image model 5 which corresponds to the subject 1 and which is marked with the surgical target site 42.

In step S3, the image capturing device 34 captures the real-time image 1' of the subject 1. Then, the image-registration module 332 performs image registration to superimpose the 3D image model 5 on the real-time image 1' so as to result in the combined image 6 which is marked with the surgical target site 42, and displays the combined image 6 via the display 31.

In step S4, the guiding-line-generating module 333 determines, based on the medical images and the surgical target site 42 marked on the combined image 6, the virtual entry site 43' that is located on the combined image 6 and that corresponds to the actual entry site 43 on the subject 1. Then, the guiding-line-generating module 333 connects the surgical target site 42 and the virtual entry site 43' with the straight line 44, generates the guiding path 45 extending from the virtual entry site 43', in the direction away from the surgical target site 42 and along the straight line 44, and displays the guiding path 45 via the display 31 for guiding the surgical instrument 7.

The instrument-tracking procedure includes steps S22 to S24 as delineated below.

In step S22, the instrument-tracking module 334 determines whether the instrument image 7' of the surgical instrument 7 appears in the combined image 6. When it is determined that the instrument image 7' of the surgical instrument 7 appears in the combined image 6, a flow of procedure proceeds to step S23. Otherwise, the flow returns to step S22 and step 22 is executed again.

In step S23, the instrument-tracking module 334 makes the first determination as to whether the tip 71' of the instrument image 7' lies on the virtual entry site 43', makes the second determination as to whether the tip 71' of the instrument image 7' reaches the surgical target site 42, makes the third determination as to whether the longitudinal axis of the instrument image 7' lies on the guiding path 45, and makes the fourth determination as to whether the instrument image 7' moves along the guiding path 45. Next, the flow proceeds to step S24.

In step S24, the instrument-tracking module 334 generates feedback based on any one of the results of the first, second, third and fourth determinations. Then, the flow returns to step S22.

A variant embodiment of the instrument-tracking procedure is similar to the aforementioned embodiment. However, in step S23 of the variant embodiment, when it is determined that the instrument image 7' appears in the combined image 6, the instrument-tracking module 334 generates the virtual instrument that corresponds to the surgical instrument 7, displays the virtual instrument in the combined image 6 at a location where the instrument image 7' appears, and makes the aforementioned first, second, third and fourth determinations.

In summary, the method according to the disclosure utilizes the system 3 to provide medical images related to a subject 1 for selecting a target image, to build a 3D image model 5 based on the medical images and a surgical target site 42 assigned to the target image, to create a combined image 6 by superimposing the 3D image model 5 on a real-time image 1' of the subject 1, to determine a virtual entry site 43' on the combined image 6 to represent an actual entry site 43 for a surgical instrument 7 to enter the subject 1, to generate a guiding path 45 that extends along a straight line 44 interconnecting the surgical target site 42 and the virtual entry site 43', and to display the guiding path 45 to serve as a guidance to movement of the surgical instrument 7 in the subject 1 to reach the surgical target site 42. In this way, a medical professional (e.g., a doctor or a surgeon) who is performing a surgical treatment on the subject 1 is able to move the surgical instrument 7 under the guidance provided by the system 3 and the method according to the disclosure, and a success rate of the surgery is thereby promoted.

In the description above, for the purposes of explanation, numerous specific details have been set forth in order to provide a thorough understanding of the embodiment. It will be apparent, however, to one skilled in the art, that one or more other embodiments may be practiced without some of these specific details. It should also be appreciated that reference throughout this specification to "one embodiment," "an embodiment," an embodiment with an indication of an ordinal number and so forth means that a particular feature, structure, or characteristic may be included in the practice of the disclosure. It should be further appreciated that in the description, various features are sometimes grouped together in a single embodiment, figure, or description thereof for the purpose of streamlining the disclosure and aiding in the understanding of various inventive aspects, and that one or more features or specific details from one embodiment may be practiced together with one or more features or specific details from another embodiment, where appropriate, in the practice of the disclosure.

While the disclosure has been described in connection with what is considered the exemplary embodiment, it is understood that this disclosure is not limited to the disclosed embodiment but is intended to cover various arrangements included within the spirit and scope of the broadest interpretation so as to encompass all such modifications and equivalent arrangements.

What is claimed is:

1. A method for guiding a surgical instrument, to be implemented by a system, the method comprising:

providing a plurality of medical images which are related to a subject for selection of one medical image from among the plurality of medical images as a target image, and displaying the target image, the target image containing an image portion which represents a lesion of the subject and on which a surgical target site is to be assigned;

building, based on the medical images and the target image with the surgical target site assigned, a three-dimensional (3D) image model which corresponds to the subject and which is marked with the surgical target site;

capturing a real-time image of the subject, performing image registration to superimpose the 3D image model on the real-time image so as to result in a combined image which is marked with the surgical target site, and displaying the combined image; and determining, based on the medical images and the surgical target site marked on the combined image, a first virtual entry site that is located on the combined image, connecting the surgical target site and the virtual entry site with a first straight line, generating a first guiding path extending from the first virtual entry site, in a direction away from the surgical target site and along the first straight line, and displaying the first guiding path for guiding the surgical instrument;

determining, based on an actual entry site, a second virtual entry site;

connecting the surgical target site and the second virtual entry site with a second straight line;

generating a second guiding path extending from the second virtual entry site, in a direction away from the surgical target site and along the second straight line; and displaying the second guiding path for guiding the surgical instrument.

2. The method as claimed in claim 1, wherein:

building a 3D image model includes building, based on the plurality of medical images, a first 3D model that represents an anatomical structure of the subject, and building a second 3D model that represents the surgical target site on the lesion based on the image portion contained in the target image, the surgical target site assigned on the target image and the plurality of medical images; and performing image registration includes superimposing the first 3D model and the second 3D model on the real-time image so as to result in the combined image.

3. The method as claimed in claim 1, further comprising:

determining whether an instrument image of the surgical instrument appears in the combined image; and when it is determined that the instrument image appears in the combined image, making a first determination as to whether a tip of the instrument image lies on the second virtual entry site, making a second determination as to whether the tip of the instrument image reaches the surgical target site, making a third determination as to whether a longitudinal axis of the instrument image lies on the second guiding path, making a fourth determination as to whether the instrument image moves along the second guiding path, and generating feedback based on any one of results of the first, second, third and fourth determinations.

4. The method as claimed in claim 3, wherein:

generating feedback includes generating one of visual feedback, audio feedback, tactile feedback and combinations thereof;

the visual feedback includes at least one of a color transition of an indicator or a message pop-up;

the audio feedback includes playback of a sound notification; and the tactile feedback includes vibrations emitted by a portable device.

5. The method as claimed in claim 1, further comprising:

determining whether an instrument image of the surgical instrument appears in the combined image;

when it is determined that the instrument image appears in the combined image, generating a virtual instrument that corresponds to the surgical instrument, displaying the virtual instrument in the combined image at a location where the instrument image appears, making a first determination as to whether a tip of the virtual instrument lies on the second virtual entry site, making a second determination as to whether the tip of the virtual instrument reaches the surgical target site, making a third determination as to whether a longitudinal axis of the virtual instrument lies on the second guiding path, making a fourth determination as to whether the virtual instrument moves along the second guiding path, and generating feedback based on any one of results of the first, second, third and fourth determinations.

6. The method as claimed in claim 5, wherein:

the generating feedback includes generating one of visual feedback, audio feedback, tactile feedback and combinations thereof;

the visual feedback includes at least one of a color transition of an indicator or a message pop-up;

the audio feedback includes playback of a sound notification; and the tactile feedback includes vibrations emitted by a portable device.

7. A system for guiding a surgical instrument, said system comprising:

a display;

a storage configured to store a plurality of medical images which are related to a subject;

an image capturing device configured to capture a real-time image of the subject; and a processor electrically connected to said storage, said display and said image capturing device, and configured to select one medical image from among the plurality of medical images as a target image and to display the target image via said display, the target image containing an image portion which represents a lesion of the subject, wherein said processor is further configured to, based on a user selection inputted via a graphical user interface (GUI), assign a surgical target site on the image portion of the target image, wherein said processor includes a model-building module, an image-registration module and a guiding-line-generating module, wherein said model-building module is configured to build, based on the medical images, a 3D image model which corresponds to the subject and which is marked with the surgical target site, wherein said image-registration module is configured to
determine whether the real-time image is being displayed via said display,
perform, when it is determined that the real-time image is being displayed via said display, image registration to superimpose the 3D image model on the real-time image so as to result in a combined image which is marked with the surgical target site, and
display the combined image via said display, and
wherein said guiding-line-generating module is configured to
determine, based on the medical images stored in said storage and the surgical target site marked on the combined image, a first virtual entry site that is located on the combined image,
connect the surgical target site and the first virtual entry site with a first straight line,
generate a first guiding path extending from the first virtual entry site, in a direction away from the surgical target site and along the first straight line, and
display the first guiding path via said display for guiding the surgical instrument
determine, based on an actual entry site, a second virtual entry site;
connect the surgical target site and the second virtual entry site with a second straight line;
generate a second guiding path extending from the second virtual entry site, in a direction away from the surgical target site and along the second straight line; and
display the second guiding path for guiding the surgical instrument.

8. The system as claimed in claim 7, wherein:
said model-building module is configured to build, based on the plurality of medical images, a first 3D model that represents an anatomical structure of the subject, and build a second 3D model that represents the surgical target site on the lesion based on the image portion contained in the target image, the surgical target site assigned on the target portion and the plurality of medical images; and
said image-registration module is configured to superimpose the first 3D model and the second 3D model on the real-time image so as to result in the combined image.

9. The system as claimed in claim 7, wherein said processor further includes:
an instrument-tracking module configured to
determine whether an instrument image of the surgical instrument captured by said image capturing device appears in the combined image, and when it is determined that the instrument image appears in the combined image,
make a first determination as to whether a tip of the instrument image lies on the second virtual entry site,
make a second determination as to whether the tip of the instrument image reaches the surgical target site,
make a third determination as to whether a longitudinal axis of the instrument image lies on the second guiding path,
make a fourth determination as to whether the instrument image moves along the second guiding path, and
generate feedback based on any one of results of the first, second, third and fourth determinations.

10. The system as claimed in claim 9, wherein:
the feedback thus generated includes one of visual feedback, audio feedback, tactile feedback and combinations thereof;
the visual feedback includes at least one of a color transition of an indicator or a message pop-up;
the audio feedback includes playback a sound notification; and
the tactile feedback includes vibrations emitted by a portable device.

11. The system as claimed in claim 7, wherein said processor further includes:
an instrument-tracking module configured to
determine whether an instrument image of the surgical instrument captured by said image capturing device appears in the combined image, and
when it is determined that the instrument image appears in the combined image,
generate a virtual instrument that corresponds to the surgical instrument,
display in the combined image via said display the virtual instrument that is placed at a location where the instrument image appears,
make a first determination as to whether a tip of the virtual instrument lies on the second virtual entry site,
make a second determination as to whether the tip of the virtual instrument reaches the surgical target site,
make a third determination as to whether a longitudinal axis of the virtual instrument lies on the second guiding path,
make a fourth determination as to whether the virtual instrument moves along the second guiding path, and
generate feedback based on any one of results of the first, second, third and fourth determinations.

12. The system as claimed in claim 11, wherein:
the feedback thus generated includes one of visual feedback, audio feedback, tactile feedback and combinations thereof;
visual feedback includes at least one of a color transition of an indicator or a message pop-up;
the audio feedback includes playback a sound notification; and
the tactile feedback includes vibrations emitted by a portable device.

13. A computer program product for guiding a surgical instrument, the computer program product comprising a non-transitory computer readable storage medium having program instructions stored therewith, the program instructions constitute a model-building module, an image-registration module and a guiding-line-generating module, the program instructions being executable by a system to cause the system to:
provide a plurality of medical images which are related to a subject for selection of one medical image from among the plurality of medical images as a target image, and display the target image, the target image containing an image portion which represents a lesion of the subject and on which a surgical target site is to be assigned;
build, by the model-building module based on the medical images and the target image with the surgical target site assigned, a 3D image model which corresponds to the subject and which is marked with the surgical target site;
capture a real-time image of the subject;
by the image-registration module, perform image registration to superimpose the 3D image model on the real-time image so as to result in a combined image which is marked with the surgical target site, and display the combined image; and
    by the guiding-line-generating module,
        determine, based on the medical images and the surgical target site marked on the combined image, a first virtual entry site that is located on the combined image,
        connect the surgical target site and the first virtual entry site with a first straight line,
        generate a first guiding path extending from the first virtual entry site in a direction away from the surgical target site and along the first straight line, and
        display the first guiding path for guiding the surgical instrument
        determine, based on an actual entry site, a second virtual entry site;
        connect the surgical target site and the second virtual entry site with a second straight line;
        generate a second guiding path extending from the second virtual entry site, in a direction away from the surgical target site and along the second straight line; and
        display the second guiding path for guiding the surgical instrument.

14. The computer program product as claimed in claim 13, wherein the program instructions further constitute an instrument-tracking module, the program instructions being executable by the system to further cause the system to, by the instrument-tracking module:
    determine whether an instrument image of the surgical instrument appears in the combined image; and
    when it is determined that the instrument image appears in the combined image,
    make a first determination as to whether a tip
    of the instrument image lies on the second virtual entry site,
    make a second determination as to whether the tip of the instrument image reaches the surgical target site,
    make a third determination as to whether a longitudinal axis of the instrument image lies on the second guiding path,
    make a fourth determination as to whether the instrument image moves along the second guiding path, and
    generate feedback based on any one of results of the first, second, third and fourth determinations.

15. The computer program product as claimed in claim 14, wherein:
    the feedback thus generated includes one of visual feedback, audio feedback, tactile feedback and combinations thereof;
    the visual feedback includes at least one of a color transition of an indicator or a message pop-up;
    the audio feedback includes playback of a sound notification; and
    the tactile feedback includes vibration emitted by a portable device.

16. The computer program product as claimed in claim 13, wherein the program instructions further constitute an instrument-tracking module, the program instructions being executable by the system to further cause the system to, by the instrument-tracking module:
    determine whether an instrument image of the surgical instrument appears in the combined image; and
    when it is determined that the instrument image appears in the combined image,
    generate a virtual instrument that corresponds to the surgical instrument,
    display in the combined image the virtual instrument that is placed at a location where the instrument image appears,
    make a first determination as to whether a tip of the virtual instrument lies on the second virtual entry site,
    make a second determination as to whether the tip of the virtual instrument reaches the surgical target site,
    make a third determination as to whether a longitudinal axis of the virtual instrument lies on the second guiding path,
    make a fourth determination as to whether the virtual instrument moves along the second guiding path, and
    generate feedback based on any one of results of the first, second, third and fourth determinations.

17. An application-specific integrated circuit (ASIC) for guiding a surgical instrument, said ASIC comprising a model-building module, an image-registration module and a guiding-line-generating module, said ASIC being utilized by an electronic device to cause the electronic device to:
    provide a plurality of medical images which are related to a subject for selection of one medical image from among the plurality of medical images as a target image, and display the target image, the target image containing an image portion which represents a lesion of the subject and on which a surgical target site is to be assigned;
    build, by the model-building module based on the medical images and the target image with the surgical target site assigned, a 3D image model which corresponds to the subject and which is marked with the surgical target site;
    capture a real-time image of the subject;
    by said image-registration module, perform image registration to superimpose the 3D image model on the real-time image so as to result in a combined image which is marked with the surgical target site, and display the combined image; and
    by said guiding-line-generating module,
        determine, based on the medical images and the surgical target site marked on the combined image, a first virtual entry site that is located on the combined image,
        connect the surgical target site and the first virtual entry site with a first straight line,
        generate a first guiding path extending from the first virtual entry site in a direction away from the surgical target site and along the first straight line, and
        display the first guiding path for guiding the surgical instrument
        determine, based on an actual entry site, a second virtual entry site;
        connect the surgical target site and the second virtual entry site with a second straight line;
        generate a second guiding path extending from the second virtual entry site, in a direction away from the surgical target site and along the second straight line; and
        display the second guiding path for guiding the surgical instrument.

18. The ASIC as claimed in claim 17, further comprising an instrument-tracking module, said ASIC being utilized by the electronic device to further cause the electronic device to, by said instrument-tracking module:
    determine whether an instrument image of the surgical instrument appears in the combined image; and when it is determined that the instrument image appears in the combined image, make a first determination as to whether a tip of the instrument image lies on the second virtual entry site, make a second determination as to whether the tip of the instrument image reaches the surgical target site, make a third determination as to whether a longitudinal axis of the instrument image lies on the second guiding path, make a fourth determination as to whether the instrument image moves along the second guiding path, and generate feedback based on any one of results of the first, second, third and fourth determinations.

19. The ASIC as claimed in claim 18, wherein:

the feedback thus generated includes one of visual feedback, audio feedback, tactile feedback and combinations thereof;

the visual feedback includes at least one of a color transition of an indicator or a message pop-up;

the audio feedback includes playback of a sound notification; and the tactile feedback includes vibrations emitted by a portable device.

20. The ASIC as claimed in claim 17, further comprising an instrument-tracking module, said ASIC being utilized by the electronic device to further cause the electronic device to, by said instrument-tracking module:

determine whether an instrument image of the surgical instrument appears in the combined image; and when it is determined that the instrument image appears in the combined image, generate a virtual instrument that corresponds to the surgical instrument, display in the combined image the virtual instrument that is placed at a location where the instrument image appears, make a first determination as to whether a tip of the virtual instrument lies on the second virtual entry site, make a second determination as to whether the tip of the virtual instrument reaches the surgical target site, make a third determination as to whether a longitudinal axis of the virtual instrument lies on the second guiding path, make a fourth determination as to whether the virtual instrument moves along the second guiding path, and generate feedback based on any one of results of the first, second, third and fourth determinations.

* * * * *